United States Patent
Olach et al.

(10) Patent No.: US 10,267,781 B2
(45) Date of Patent: Apr. 23, 2019

(54) SYSTEM FOR DETERMINING CHLORINE DEMAND IN WATER

(71) Applicants: Yaroslav Olach, New York, NY (US); Viktor Gribenko, Brooklyn, NY (US)

(72) Inventors: Yaroslav Olach, New York, NY (US); Viktor Gribenko, Brooklyn, NY (US)

( * ) Notice: Subject to any disclaimer, the term of this patent is extended or adjusted under 35 U.S.C. 154(b) by 247 days.

(21) Appl. No.: 15/194,388

(22) Filed: Jun. 27, 2016

(65) Prior Publication Data

US 2017/0370892 A1 Dec. 28, 2017

(51) Int. Cl.
*G01N 33/18* (2006.01)
*G01N 21/78* (2006.01)
*G01N 21/90* (2006.01)

(52) U.S. Cl.
CPC .......... *G01N 33/182* (2013.01); *G01N 21/78* (2013.01); *G01N 21/90* (2013.01)

(58) Field of Classification Search
CPC .......... G01N 33/182; G01N 35/00871; G01N 35/1097; G01N 21/78; G01N 2035/00891; G01N 2035/009
See application file for complete search history.

(56) References Cited

U.S. PATENT DOCUMENTS

| 4,940,946 | A | | 7/1990 | Nazaryan | |
|---|---|---|---|---|---|
| 5,352,363 | A | * | 10/1994 | Shibano | B01D 17/042 210/651 |
| 7,985,377 | B2 | | 7/2011 | Vincent | |
| 2001/0004962 | A1 | * | 6/2001 | Hirota | C02F 1/46104 204/228.1 |
| 2002/0162802 | A1 | * | 11/2002 | Simmons | C02F 1/686 210/739 |
| 2005/0218054 | A1 | * | 10/2005 | Sakata | A61L 2/18 210/192 |

(Continued)

FOREIGN PATENT DOCUMENTS

| CN | 201724839 U | 1/2011 |
|---|---|---|
| CN | 203870025 U | 10/2014 |
| JP | 2000-180432 | 6/2000 |

OTHER PUBLICATIONS

"Chlorine Demand Analyzer," http://www.analyticon.com/products/water-washwater-process-monitors/Chlorine-Demand-Analyzer.php (last accessed on Oct. 15, 2015), 2 pgs.

*Primary Examiner* — Matthew D Krcha
(74) *Attorney, Agent, or Firm* — Richard C. Litman

(57) ABSTRACT

The system for determining chlorine demand in water includes a reagent supply tank configured for holding a solution of sodium hypochlorite of known concentration, a buffer tank positioned in fluid communication with the reagent supply tank, the buffer tank including a first conduit configured for transferring the solution from the reagent supply tank into the buffer tank, and a mixing tank positioned in fluid communication with the buffer tank, the mixing tank including a second conduit configured for transferring the solution from the buffer tank into the mixing tank to form a composite solution. The system further includes a first chlorine measuring device for measuring the free chlorine residual in a water source connected to the mixing tank, a second chlorine measuring device configured for measuring the free chlorine residual in the composite solution, and a pump operatively coupled to the water source.

5 Claims, 2 Drawing Sheets

(56) References Cited

U.S. PATENT DOCUMENTS

| | | | |
|---|---|---|---|
| 2011/0198238 A1* | 8/2011 | Lee .................... | C02F 1/46109 |
| | | | 205/760 |
| 2011/0284475 A1* | 11/2011 | Kolodny ................. | C02F 1/004 |
| | | | 210/748.02 |
| 2016/0377583 A1* | 12/2016 | Takahashi ............ | G01N 33/182 |
| | | | 436/124 |

* cited by examiner

SYSTEM FOR DETERMINING CHLORINE DEMAND IN WATER

BACKGROUND OF THE INVENTION

1. Field of the Invention

The present invention relates to water quality testing, and particularly to a system for determining chlorine demand in water.

2. Description of the Related Art

The quality of water is typically characterized by pH, odor, turbidity (below 1.5 NTU), concentration of fluoride (0.80% mg/L), concentration of phosphoric acid (2.0 mg/L), conductivity, as well as temperature. Water is typically disinfected by the used of ultraviolet light and chlorine (the free chlorine residue as set forth by EPA regulation is approximately 0.20 mg/L in taps of a city distribution system).

Chlorine is and has been used for many years to eliminate a large variety of microbial waterborne pathogens, including those that can cause typhoid fever, dysentery, cholera and Legionnaires' disease. Chlorination improves and preserves drinking water throughout many of the developed nations around the world. However, chlorine is not only expensive to manufacture, it can also be deadly to human beings if the amount of chlorine deposited in drinking water is not properly measured.

While a certain amount of chlorine in drinking water can destroy bacteria and be safe for people to drink, too much chlorine in drinking water can lead to peculiar taste and odors in the drinking water, unhealthy by-products, and, ultimately, death, such as by cancer. As such, the concentrations levels of chlorine in potable water must be accurately controlled to maintain safety and the quality of the drinking water. As public awareness of water quality increases, and water quality become a concern, monitoring of water quality, including the chlorine concentration, is becoming more and more common.

While the chlorine demand in potable water can fluctuate based on the pH level and temperature of the water, it mainly revolves around the turbidity of the potable water, the organic impurities (create foul odors), and the concentration of ammonia, which together account for 99% of the quality of water. For municipal water treatment plants, chlorine demand meters are an additional way to control water quality. For example, chlorine demand meters for municipal water quality control can determine the efficacy of the filtration plant that reduces turbidity and organic contents. Moreover, for individuals who use filters at home, chlorine demand meters can determine the efficacy of such filters.

The accuracy, however, of determining chlorine demand is a common problem in chlorine demand meters that are currently on the market, since the flow rates of treated water and disinfectant chemicals are unstable. Meters are typically inaccessible once they are installed, and cannot be calibrated correctly or as often as may be required to maintain a certain level of quality. Further, the industrial hypochlorite used for disinfection tends to lose strength and efficiency as time progresses. For example, a solution containing 12.5% hypochlorite can lose 50% of its strength in approximately eighty (80) days. Not knowing the correct strength of the hypochlorite solution can cause people to overestimate the amount of chlorine needed (i.e., the chlorine demand) to disinfect the water. Also, chlorine meters currently utilized for municipal water supplies can also be very difficult to operate and very expensive to repair.

Thus, a system for determining chlorine demand in water solving the aforementioned problems is desired.

SUMMARY OF THE INVENTION

The system for determining chlorine demand in water includes a tank configured for holding a solution, a buffer tank positioned in fluid communication with the tank, the buffer tank including a first conduit configured for transferring the solution from the tank into the buffer tank, and a mixing tank positioned in fluid communication with the buffer tank, the mixing tank including a second conduit configured for transferring the solution from the buffer tank into the mixing tank to form a composite solution.

The system further includes a first chlorine measuring device operatively coupled to a water source, the first chlorine measuring device being configured for measuring the free chlorine residual in the water source, and a second chlorine measuring device operatively coupled to the mixing tank, the second chlorine measuring device being configured for measuring the free chlorine residual in the composite solution, wherein the measurement of the first chlorine measuring device is compared with the measurement of the second chlorine measuring device to determine the amount of chlorine to mix into the water to increase the water quality. The chlorine measuring device(s) may be a pocket colorimeter for portable operation, or an automated residual chlorine analyzer for stationary operation. A pump is operatively coupled to the mixing tank, the pump being configured for propelling the water through the system.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
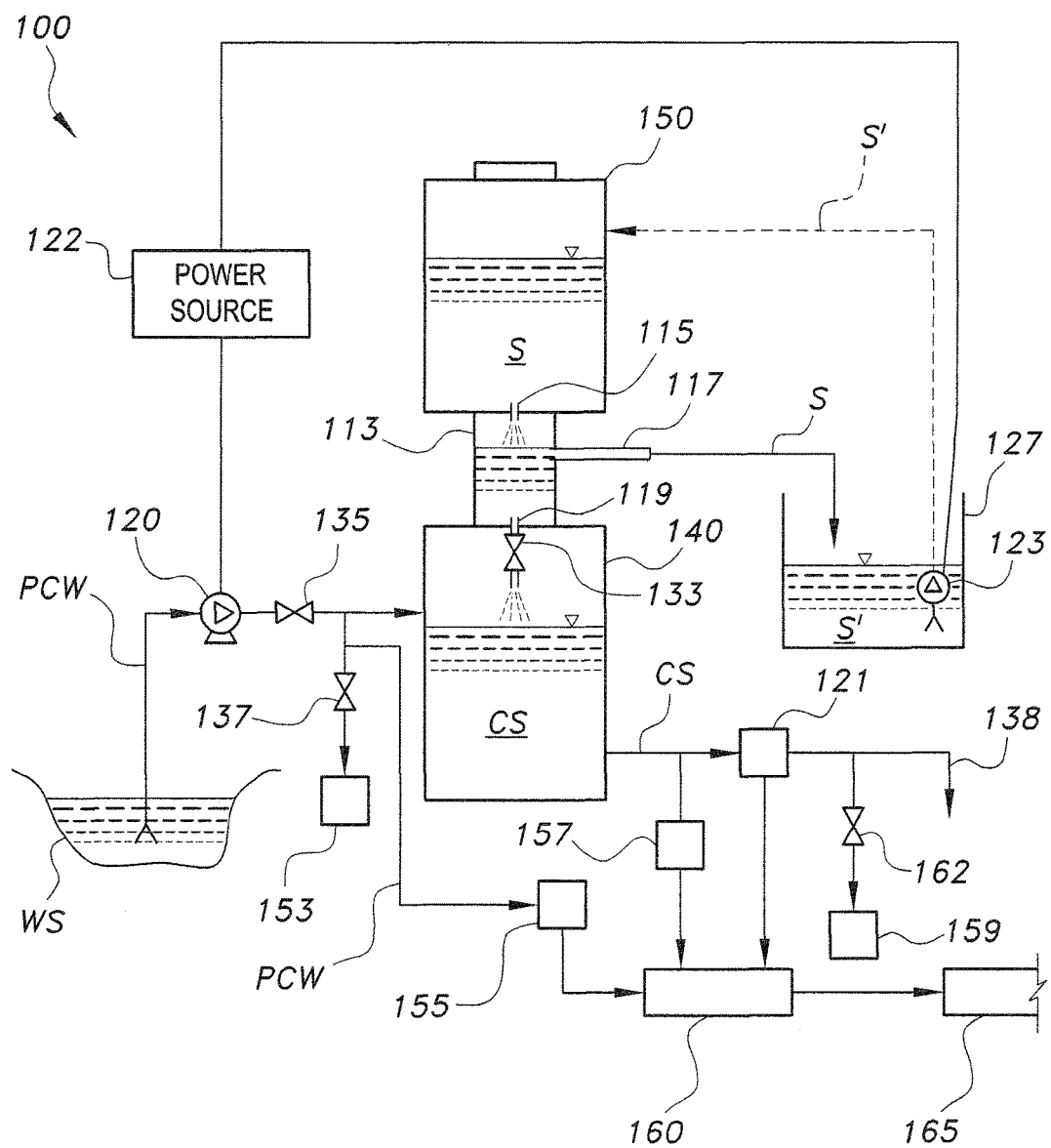
FIG. 1 is a schematic diagram of a system for determining chlorine demand according to the present invention.

Referring to FIG. 1, a system 100 for determining chlorine demand for water from a water supply WS is generally illustrated. Chlorine may be added to a water supply at a water purification plant directly in the form of chlorine gas, but is more commonly added in a water soluble reagent, such as sodium hypochlorite (NaOCl). The amount of chlorine added is referred to as the dosage. A certain amount of the dosage reacts with bacteria or harmful organic matter to disinfect the water and make the water potable and safe for use. This is referred to as the chlorine demand. The chlorine demand is used up in the process of disinfecting or treating the water, and is no longer available if the water is re-infected. The process of disinfecting or treating the water requires a certain amount of reaction time or contact time, so the chlorine demand is time-dependent. Any remaining chlorine is referred to as the total chlorine or residual chlorine. Residual chlorine includes free chlorine and combined available chlorine. Free chlorine is usually present in the form of hypochlorous acid or hypochlorite ions, and is readily available to treat harmful pathogens introduced into the water after initial treatment. Combined available chlorine includes chlorine that has combined with ammonia or nitrogenous organic compounds in the water, generally referred to as chloramines. It is considered desirable to leave, a certain percentage of free chlorine in treated water after the initial reaction or dwell time, enough to provide some level of protection, but not enough to be harmful or offensive. Given the varying composition of water in a river, stream, or lake, it is often necessary to continuously or periodically monitor the chlorine demand and adjust the dosage of chlorine treatment.

The system 100 shown in FIG. 1 can be configured to be portable or stationary. The system includes a reagent supply tank 150 capable of holding between 4 liters of a solution S of sodium hypochlorite of known concentration for a portable configuration, or 19 liters of the solution S for a stationary configuration. A buffer tank 113 is positioned in fluid communication with the tank 150, the buffer tank 113 being configured for receiving the solution S via a first conduit 115 disposed between the tank 150 and the buffer tank 113, the first conduit 115 providing a flow of solution S, which depends on the level of solution in tank 150, into the buffer tank 113. A mixing tank 140 is positioned in fluid communication with the buffer tank 113, the mixing tank 140 being configured for receiving the solution S from the buffer tank 113 via a second conduit 119 disposed between the buffer tank 113 and the mixing tank 140, and for receiving pre-chlorinated water PCW (e.g., tap water) from the water source WS in order to mix the solution S with the pre-chlorinated water PCW and form a composite solution CS.

The first conduit 115 may have a diameter of 2 mm, and the second conduit 119 may have a diameter less than the diameter of the first conduit 115, such as a diameter of 1 mm, to maintain a constant amount of solution S in the buffer tank 113, which, in turn, can provide a flow of solution S into the mixing tank 140. The second conduit 119 may include a regulator 133 or metering device configured for precisely controlling the flow of solution S into the mixing tank 140. The flow of solution S may be between 0 and 20 ml/minute, depending on the concentration of the solution S and the measurement of free chlorine in the pre-chlorinated water PCW from the water source WS. The regulator 133 may be configured to regulate the dosage of disinfectant into the pre-chlorinated water PCW according to these flow rates.

The buffer tank 113 also includes an overflow tube 117 disposed on one side of the buffer tank 113 for discharging any excess solution S above a predetermined level to maintain a constant level of solution S in the buffer tank 113. The overflow tube 117 discharges the excess solution S' above the predetermined level into an overflow tank 127 configured to hold the excess solution S'. The first conduit 115 and the overflow tube 117 maintain a constant level in the buffer tank 113, and accordingly, a constant flow through the second conduit 119 and the regulator 133 to the mixing tank 140. The overflow tank 127 may include a pump 123 configured to recirculate the excess solution S' into the tank 150 so that the excess solution S' can be reused, the pump 123 being operatively coupled to a power source 122, such as a battery, a generator, solar panels, a wind turbine, or a water turbine. It is to be noted that the solution S and the excess solution S' have the same concentration.

For portable operation, a first colorimeter 153 may be operatively coupled to the water source WS through a sampling tap, and a second colorimeter 159 may be operatively coupled to the mixing tank 140 through a second sampling tap, the colorimeters 153, 159 being configured to measure the absorbance of particular wavelengths of light to determine the concentration of a known solute in a given solution, such as by the application of the Beer-Lambert principle.

A first regulator 135 is operatively coupled to the water source WS, a second regulator 137 is operatively coupled to the first regulator 135, and a third regulator 162 is operatively coupled to the mixing tank 140. The regulators or valves 135, 137, 162 are configured to control the flow of pre-chlorinated water PCW and composite solution CS, respectively, throughout the system 100. For example, the first regulator 135 controls the flow of a portion of the pre-chlorinated water PCW from the water source WS into the mixing tank 140, the second regulator 137 controls the flow of a portion of the pre-chlorinated water PCW through the first tap into the first colorimeter 153, and the third regulator 162 controls the flow of a portion of the composite solution CS through the second tap into the second colorimeter 159.

For stationary operation, a first chlorine meter 155 may be connected to the first tap to sample the water source WS, the first chlorine meter 155 being configured for measuring the free chlorine in the pre-chlorinated water PCW. A second chlorine meter 157 may be connected to the second tap to sample water output from the mixing tank 140, the second chlorine meter 157 being configured for measuring the free chlorine of the composite solution CS from the mixing tank 140. The system 100 includes a pump 120 operatively coupled to the power source 122 to propel the pre-chlorinated water PCW from the water source WS through the first regulator 135 and into the mixing tank 140, or alternatively, through the second regulator 137 into the first colorimeter 153. It is to be noted that a portion of the pre-chlorinated water PCW can also be diverted into the first chlorine meter 155.

A control device 160 positioned in communication with the first chlorine meter 155 and in communication with the second chlorine meter 157 is configured for comparing the free chlorine of the pre-chlorinated water PCW and the free chlorine of the composite solution and calculating the chlorine demand. Once the control device 160 calculates the correct chlorine demand, the control device 160 can adjust the regulators 135, 137, 162 accordingly. The control device 160 can also be configured to adjust the regulator 133 in the second conduit 119 disposed between the buffer tank 113 to the mixing tank 140.

The control device 160, such as a standalone computer, computer terminal, portable computing device, networked computer or computer terminal, or networked portable device, and can also include a microcontroller, an application specific integrated circuit (ASIC), or a programmable logic controller (PLC). The control device 160 includes a display 165 to indicate the concentration of free chlorine in the pre-chlorinated water (PCW), as well as the concentration of free chlorine in the composite solution CS.

It is to be understood that if the system 100 is being used as a portable system, the first chlorine meter 155 and the second chlorine meter 157, as well as the control device 160 and the second pump 123, can be removed. If, on the other hand, the system 100 is being used as a stationary system, instead of using the first colorimeter 153 and the second colorimeter 159, the chlorine meters 155, 157, such as HACH or SEIMENS manufactured chlorine meters or analyzers (e.g., the Hach CL17 or the Siemens SFC series analyzers), the control device 160 and corresponding display 165 can be utilized. Additionally, if the system is being used as a stationary system, the second pump 123 for recirculating the excess solution S' can also be utilized.

Figure 2:
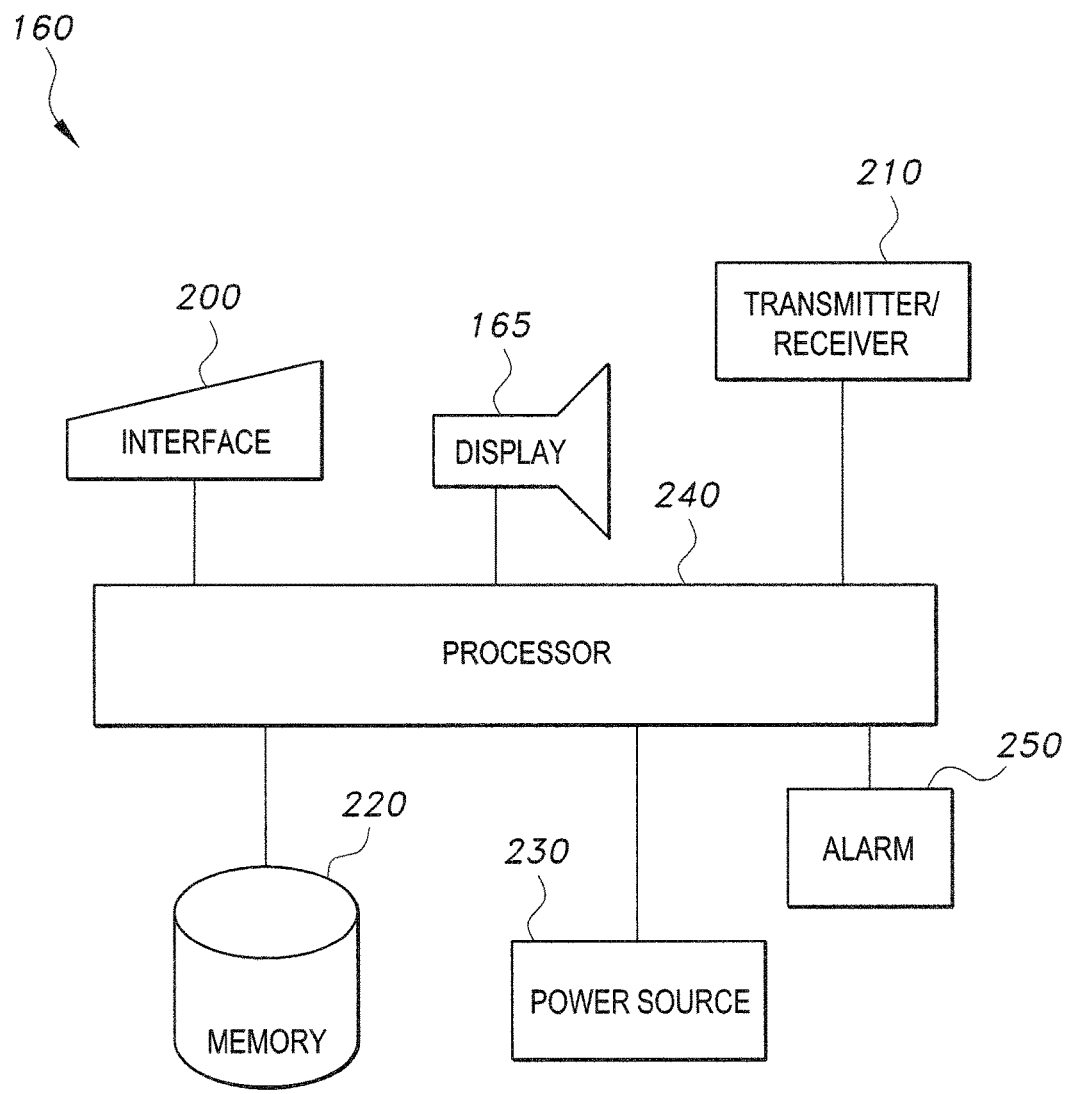
FIG. 2 is a block diagram of a generalized system of a control device for use with the system for determining chlorine demand of FIG. 1.

Referring to FIG. 2, data can be entered into the control device 160 by a user, or sent or received from or by one of the colorimeters 153, 159 or one of the chlorine meters 155, 157 via any suitable type of interface 200 that can be associated with a transmitter/receiver 210, such as for wireless transmission/reception or for wireless communication. The transmitter/receiver 210 can send or receive data or control signals sent or received by or from the control device 160. The control device 160 can include a memory 220 to store data and information, as well as program(s) or instructions for varying the amount of solution S deposited into the pre-chlorinated water PCW to not only maintain, if not improve, the quality of the pre-chlorinated water PCW, but also to ensure that the pre-chlorinated water PCW is safe for consumption. Additionally, the control panel 160 can include an alarm 250 configured for alerting users to an issue and for displaying on the display 165 warning messages, such as "Danger High Demand!" if the chlorine demand is greater than 2.00 parts per million (ppm) (as recently occurred in Flint, Mich.) and messages, such as "Caution Negative Demand. Overfeeding!" if the chlorine demand is below 0.00 ppm. It is to be noted that the alerts can be sent to all users of the system 100.

The memory 210 can be any suitable type of computer readable and programmable memory, such as non-transitory computer readable media, random access memory (RAM) or read only memory (ROM). The control device 160 can also be powered by a power source 230, such as a battery.

Calculations, determinations, data transmission or data reception, sending or receiving of control signals or commands, such as in relation to increasing or decreasing the amount of solution S deposited into the pre-chlorinated water PCW, or providing information such as temperature of the water, etc., are performed or executed by a processor 240 of the control device 160. The processor 240 can be any suitable type of computer processor, such as a microprocessor or an ASIC, and the calculations, determinations, data transmission or data reception, sending or receiving of control signals or commands processed or controlled by the processor 240 can be displayed to the user of the control device 160 on the display 165, which can be any suitable type of computer display, such as a light emitting diode (LED) or liquid crystal display (LCD).

The processor 240 can be associated with or incorporated into any suitable type of computing device, for example, a personal computer or a PLC. The display 165, the processor 240, the transmitter/receiver 210, the memory 220, and any associated computer readable media are in communication with one another by any suitable type of data bus, as is well known in the art.

By way of operation, the water from a water supply WS, such as a municipal water supply, including lakes, rivers, and wells, is first treated with a certain amount of chlorine, fluoride, and ultraviolet lights. Subsequently, a portion of the pre-chlorinated water PCW is propelled by the pump 120 of the system 100 through the first regulator 135 into the mixing tank 140, where the pre-chlorinated water PCW is mixed with the solution S, such as a low known concentration of sodium hypochlorite solution specially prepared by an industrial hypochlorite supplier. The concentration of solution S can be adjusted beforehand according to the constant flow of solution S through the second conduit 119 into the mixing tank 140 and the constant flow of pre-chlorinated water PCW into the mixing tank 140 to form the correct composite solution CS. The main idea of the preparation procedure, described above, is to know the concentration of the free chlorine $C_f$ created by a known flow of solution S through the second conduit 119 into a given amount of water with chlorine demand (D) equal to 0 flowing into the mixing tank 140. The solution S is contained in the tank 150 and flows through the buffer tank 113 and into the mixing tank 140. It is to be noted that the concentration of hypochlorite can be controlled at any time during the inspection of the pre-chlorinated water PCW.

The pump 120 of the system 100 also propels a portion of the pre-chlorinated water PCW through the first regulator 135 and through the second regulator 137 into the first colorimeter 153 or to the first chlorine meter 155, where the free chlorine residual $C_p$ in the pre-chlorinated water PCW can be determined and sent via wireless communication to the control device 160 or entered manually.

While in the mixing tank 140, the pre-chlorinated water PCW can be mixed with the solution S contained in the buffer tank 113 storing the solution S, as described herein. It is to be understood that the amount of solution S flowing into the buffer tank 113 and the mixing tank 140 is controlled by the first conduit 115 and the second conduit 119, respectively. The amount of solution S flowing into the mixing tank 140 can be further controlled by the regulator 133 positioned in the second conduit 119 disposed between the buffer tank 113 and the mixing tank 140. Once the solution S and the pre-chlorinated water PCW are mixed to form the composite solution CS, a portion of the composite solution CS is propelled into the second colorimeter 159 or the second chlorine meter 157, which can determine the free chlorine residual $C_f$ in the composite solution CS. The results from the second colorimeter or second chlorine meter 157 can then be transmitted to the control device 160 or entered manually for further analysis and comparison to the free chlorine residual $C_p$ from the pre-chlorinated water PCW from the first colorimeter 153 and the first chlorine meter 155.

The remaining portion of the composite solution CS can be propelled into a water flow meter 121 positioned in fluid communication with the mixing tank 140. The remaining portion of the composite solution CS can be drained out of the device 100 through an outlet tube 138.

Various tests have been done in Ukraine and in the United States of America, the results of which are illustrated in Table 1.

TABLE 1

Experimental results

| Location of Sampling | Type of Water | Free Cl$_2$ (ppm), C$_p$ on Inlet Water | Free Cl$_2$ (ppm), C$_f$ on Outlet Water | Dosage (ppm) to mixer, C$_a$ | Index of Quality D = C$_a$ + C$_p$ - C$_f$ |
|---|---|---|---|---|---|
| Staten Island, USA | Raw | 0.50 | 1.45 | 1.05 | +0.10, good |
| City Island, USA | Treated | 0.80 | 1.93 | 1.05 | −0.08, good |
| Yonkers, T-3, USA | Raw | 0.10 | 1.10 | 1.05 | +0.05, good |
| Poughkeepsie, USA | Raw | 0.00 | 1.10 | 2.20 | +1.1, no good |
| Poughkeepsie, USA | Raw | 0.00 | 2.20 | 2.20 | 0.00, ideal |
| Central Park, USA | Lake | 0.00 | 0.70 | 1.80 | +1.1, no good |
| 1 L of water containing 40 mL of Ammonia | | 0.00 | 0.60 | 90.00 | +89.4, no good |
| Kyiv, Ukraine (Desna River) | Treated | 0.05 | 0.53 | 2.20 | +1.72, no good |
| Cherkasy, Ukraine (Dnipro River) | Treated | 0.05 | 0.65 | 2.20 | +1.60, no good |
| Slavyansk, Ukraine (Lake in area of war) | Raw | 0.00 | 0.65 | 2.20 | +1.55, no good |
| Ternopil, Ukraine (pre - iron filtration) | Raw | 0.00 | 0.22 | 1.80 | +1.58, no good |
| Ternopil, Ukraine (post - iron filtration) | Treated | 0.15 | 1.00 | 1.80 | +0.95, good |
| Lviv, Zacarpatsk (Private Wells) | Natural | 0.00 | 2.20 | 2.20 | 0.00, ideal |

Equation 1 is used to determine value the free chlorine residual (Ca) as follows:

$$Ca = \frac{Fh}{Fw} \times Hs(\text{ppm}), \quad (1)$$

where Fh equals the flow rate of hypo solution into the mixing tank 140, Fw equals the flow rate of pre-chlorinate water PCW by the pump 120 into the mixing tank 140, and Hs=0.125×Specific gravity (Sg), wherein the Sg equals 1.18. Hs, in turn, equals 0.15 ppm of free chlorine in one million gallons of water with a chlorine demand (D) of zero.

As it relates to the system 100, the chlorine meters 155, 157 must be calibrated periodically with a prepared solution and water having a chlorine demand (D) of 0. Chlorine demand (D) represents the amount of chlorine that has reacted and has been absorbed by the impurities in the pre-chlorinated water PCW. By calibrating and re-calibrating, the accuracy of the chlorine demand meters 155, 157 can be increased.

Throughout these tests, the solution S was a 0.037% hypochlorite solution prepared from a fresh 12.5% industrial solution from H. Krevit & Company, Inc. The flow rate of the solution S was 10 ml/minute through the second conduit 119, and the flow rate of pre-chlorinated water PCW was 2 L/minute with a chlorine demand (D) of 0. The solution S with prepared known concentration Ca ppm and the pre-chlorinated water PCW with concentration Cp ppm both flowed into the mixing tank 140 to create a composite solution having Cf ppm of free chlorine. Equation 2 is used to determine the corresponding parts per million (ppm) of chlorine, as follows:

$$D = Ca + Cp - Cf, \quad (2)$$

where D equals demand of chlorine in ppm, Ca equals the free chlorine residual in ppm for prepared solution S, Cp equals the free chlorine as measured by the colorimeter 153 or chlorine meter 155 in ppm, and Cf equals the free chlorine as measured by the chlorine meter 157 or colorimeter 159 in ppm. As illustrated in Table 1, in all tests the prepared known concentration Ca ppm has different numbers and should always be controlled, depending on the freshness of industrial solution, the range of chlorine meters used, and the predicted demand. In the tests discussed herein, the solution Ca was 1.05 ppm, 1.80 ppm, 2.20 ppm and even 90.00 ppm for water containing 40.0 ml of urine. The Cp of pre-chlorinated water PCW can range from 0 ppm (from natural water) up to 0.40 ppm. The chlorine demand (D) can range from −0.5 ppm for over-chlorinated raw water to 2.0 ppm for very dirty raw water, such as the water from the Flint river that needed special long term investigation using permanently installed stationary systems at least on the inlet and outlet of the filtration plant and again at the outlet through which treated water is distributed. Additionally, portable systems could have been used to periodically test the chlorine demand of water in hydrants at various points in Flint City where lead pipes are still being utilized to detect leached lead and iron.

According to equation (2), if pre-chlorinated water PCW has a concentration of free chlorine Cp of 0.32 ppm and a concentration of free chlorine Cf of 1.8 ppm, then the chlorine demand D equals 0.52 ppm if used with a prepared solution S having a concentration of Ca equaling 2.00 ppm (D=2.00+0.32−1.80=0.52).

It is to be understood that the present invention is not limited to the embodiments described above, but encompasses any and all embodiments within the scope of the following claims.

We claim:

1. A system for determining chlorine demand in a water source, the system consisting of:
   a reagent supply tank configured for holding a solution of hypochlorite ions in known concentration;
   a buffer tank positioned in direct fluid communication with the reagent supply tank;
   a first conduit disposed between the reagent supply tank and the buffer tank, the first conduit being configured for transferring the solution from the reagent supply tank into the buffer tank via gravity;
   a mixing tank positioned in direct fluid communication with the buffer tank;
   a second conduit disposed between the buffer tank and the mixing tank, the second conduit being configured for transferring the solution from the buffer tank into the mixing tank to form a composite solution via gravity;

a plurality of metering devices located throughout the system for regulating the flow of water and composite solution, the plurality of metering devices including at least:
  i) a first metering device in direct fluid communication with the second conduit for controlling the flow of the solution into the mixing tank;
  ii) a second metering device operatively coupled to the water source and controlling the flow of the water source into the mixing tank;
  iii) a third metering device operatively coupled to the second metering device and controlling the flow of the water source from a first tap; and
  iv) a fourth metering device operatively coupled to the mixing tank and controlling the flow of the composite solution from a second tap;
a first chlorine measuring device connected to the first tap located between the water source and the mixing tank, the first chlorine measuring device being configured for measuring free chlorine in the water source;
a first pump operatively coupled to the mixing tank, the first pump being configured for pumping water from the water source into the mixing tank, the first tap being disposed between the first pump and the mixing tank;
a second chlorine measuring device connected to the second tap at an output of the mixing tank, the second chlorine measuring device being configured for measuring free chlorine in the composite solution;
a control device, the control device including a display, the control device being in communication with at least the first and second chlorine measuring devices and configured to compare the measured free chlorine in the water source and the measured free chlorine in the composite solution and to calculate and display the chlorine demand and to adjust the plurality of metering devices;
an overflow tank positioned in fluid communication with the buffer tank, the overflow tank being configured for receiving excess hypochlorite ion solution once the solution reaches above a predetermined level in the buffer tank; and
a second pump configured for recirculating the excess solution into the reagent supply tank;
wherein the reagent supply tank, the buffer tank and the mixing tank are integrated into one piece.

2. The system for determining chlorine demand in water according to claim 1, wherein the first and second chlorine measuring devices each comprise a pocket colorimeter.

3. The system for determining chlorine demand in water according to claim 1, wherein the first and second chlorine measuring devices each comprise an automated chlorine analyzer for analyzing residual chlorine in a water sample.

4. The system for determining chlorine demand in water according to claim 1, wherein each of the plurality of metering devices comprises a valve, each of the valves being configured for controlling flow of liquid through the system.

5. The system for determining chlorine demand in water according to claim 1, wherein the control device display further includes an alarm configured for alerting the system if the chlorine demand is above or below predetermined norms for the system.

* * * * *